US008353862B2

(12) United States Patent
Orilla et al.

(10) Patent No.: US 8,353,862 B2
(45) Date of Patent: Jan. 15, 2013

(54) DRUG DELIVERY SYSTEMS AND METHODS

(75) Inventors: Werhner C. Orilla, Anaheim, CA (US); James A. Burke, Santa Ana, CA (US)

(73) Assignee: Allergan, Inc., Irvine, CA (US)

( * ) Notice: Subject to any disclaimer, the term of this patent is extended or adjusted under 35 U.S.C. 154(b) by 34 days.

(21) Appl. No.: 11/934,218

(22) Filed: Nov. 2, 2007

(65) Prior Publication Data

US 2009/0118703 A1 May 7, 2009

(51) Int. Cl.
*A61M 31/00* (2006.01)

(52) U.S. Cl. .......................................... 604/57; 604/518

(58) Field of Classification Search ............... 604/60, 604/61, 164.11, 191, 218, 294, 521, 518, 604/57
See application file for complete search history.

(56) References Cited

U.S. PATENT DOCUMENTS

| 3,749,084 | A | * | 7/1973 | Cucchiara | 600/575 |
|---|---|---|---|---|---|
| 4,188,949 | A | | 2/1980 | Antoshkiw | |
| 4,476,866 | A | * | 10/1984 | Chin | 606/194 |
| 5,288,291 | A | * | 2/1994 | Teoh | 604/60 |
| 5,792,099 | A | * | 8/1998 | DeCamp et al. | 604/506 |
| 6,899,717 | B2 | | 5/2005 | Weber et al. | |
| 7,090,681 | B2 | | 8/2006 | Weber et al. | |
| 2002/0198511 | A1 | * | 12/2002 | Varner et al. | 604/521 |
| 2004/0137059 | A1 | | 7/2004 | Nivaggioli et al. | |
| 2005/0101967 | A1 | * | 5/2005 | Weber et al. | 606/107 |
| 2006/0200113 | A1 | * | 9/2006 | Haffner et al. | 606/6 |
| 2007/0088014 | A1 | | 4/2007 | Edelman | |
| 2008/0097335 | A1 | * | 4/2008 | Trogden et al. | 604/192 |
| 2008/0287913 | A1 | * | 11/2008 | Schwab | 604/518 |

FOREIGN PATENT DOCUMENTS

WO WO 03-092564 11/2003

OTHER PUBLICATIONS

Koch, F.H., Gumbel, H.O., Hattenbach, L.O., Ohrloff C., "Intravitreal Endoscopic Visualization of Intraocular Ganciclovir Devices: Improved Long-Term Treatment of CMV Retinitis", Klinische Monatsblatter fur Augenheilkunde, (Feb. 1999) vol. 214, No. 2, pp. 107-111.
Hudson, Henry L., "Retisert: A Step Forward in Treating Chronic Noninfectious Posterior Uveitis", Jul. 2005.
MacCumber, Mathew W., Sadeghi, Scott, Cohen, Jack A. Deutsch, Thomas A., "Suture Loop to Aid in Ganciclovir Implant Removal", Arch Ophthalmol. 199; 117: 1250-1254.

* cited by examiner

*Primary Examiner* — Kevin C Sirmons
*Assistant Examiner* — Brandy C Scott
(74) *Attorney, Agent, or Firm* — Louis V. Wollenberger; Joel B. German; Debra D. Condino

(57) ABSTRACT

A delivery system includes a housing along with a tip connected to one end of the housing. A first cannula extending from the tip is provided for inserting a rod implant into tissue. A second cannula, concentrically disposed within the first cannula, is utilized to force the rod implant from the first cannula and for ejecting a fluid behind the inserted rod implant in the tissue.

15 Claims, 2 Drawing Sheets

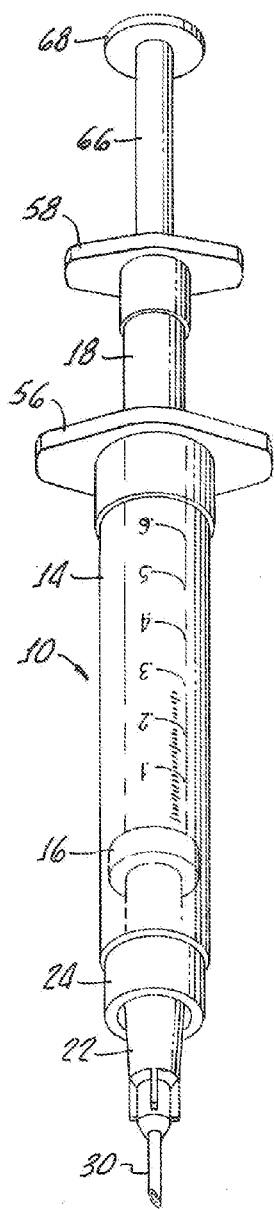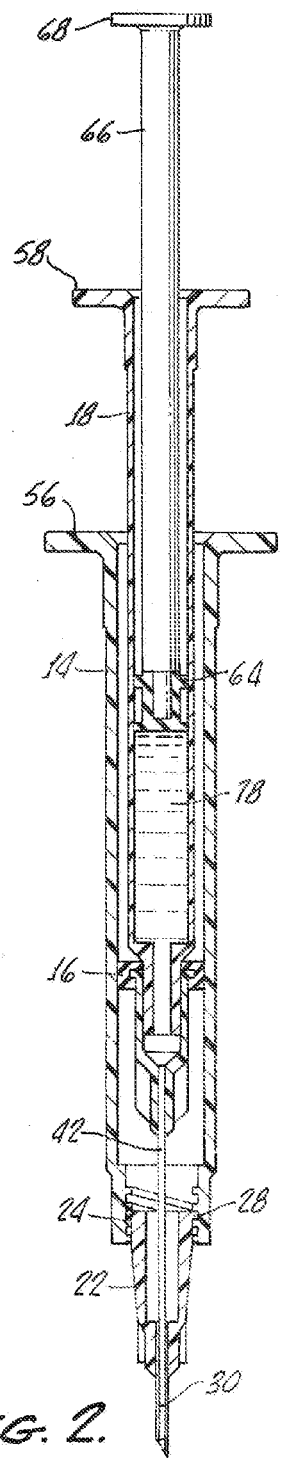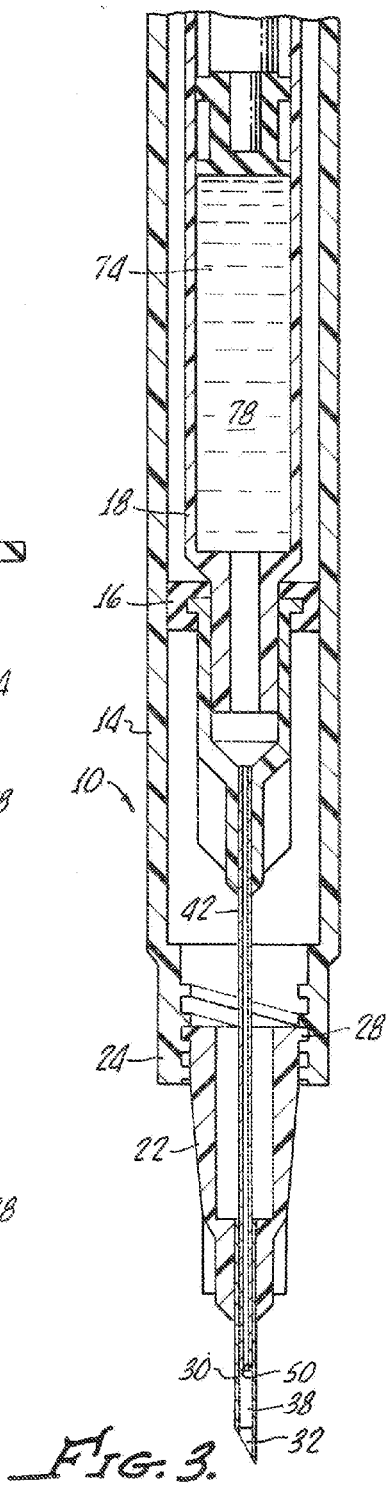
FIG. 1.
FIG. 2.
FIG. 3.

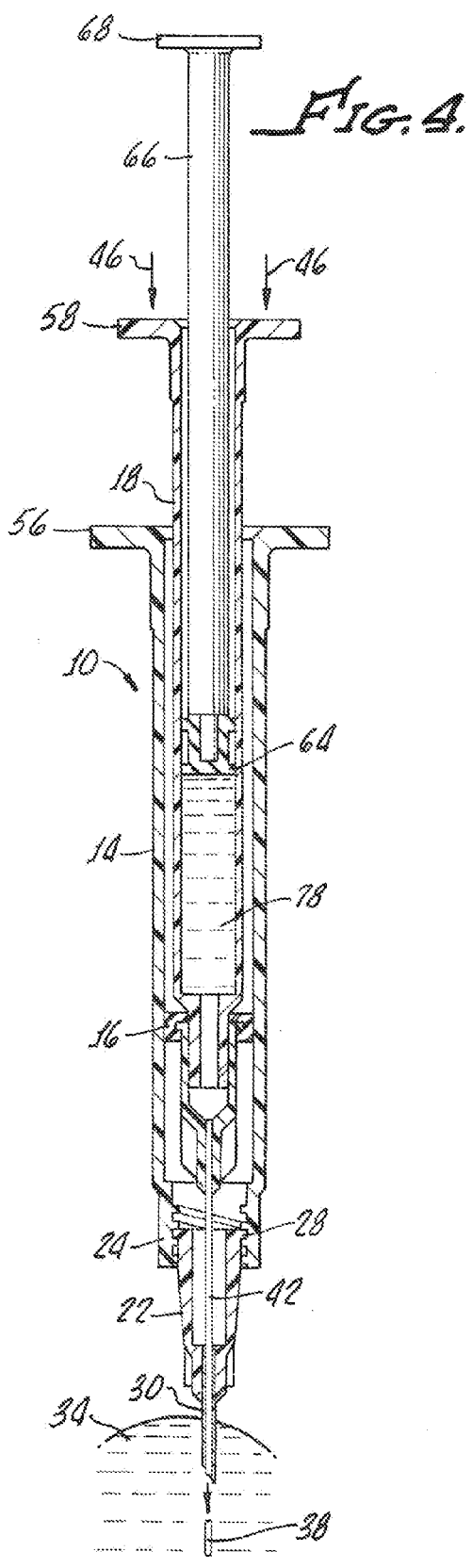
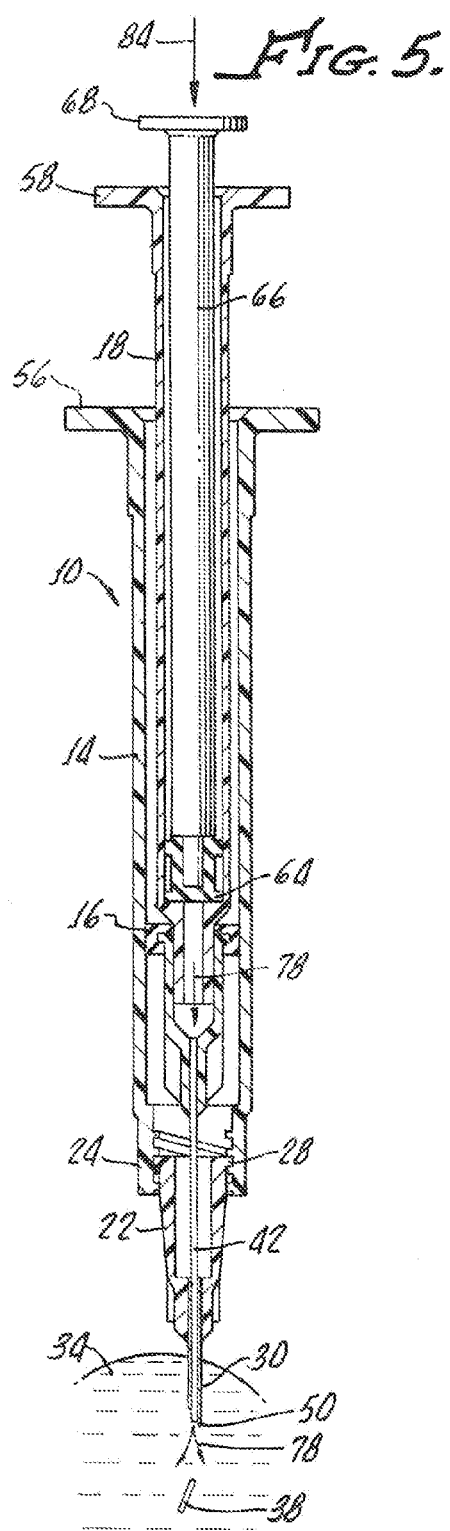

DRUG DELIVERY SYSTEMS AND METHODS

The present invention relates to methods and apparatus for delivering solid or semi-solid materials into the eye. Specifically, the present invention relates to a drug delivery system and methods that can be used to introduce implants containing therapeutic or active agents, including bioerodible implants, into various locations within the eye, including into the vitreous of the eye.

A primary difficulty in treating diseases of the eye is the inability to introduce drugs or therapeutic agents into the eye and maintain these drugs or agents at a therapeutically effective concentration in the eye for the necessary duration. Systemic administration may not be an ideal solution because, often, unacceptably high levels of systemic dosing is needed to achieve effective intraocular concentrations, with the increased incidence of unacceptable side effects of the drugs. Simple ocular instillation or application is not an acceptable alternative in many cases because the drug may be quickly washed out by tear-action or is otherwise depleted from within the eye into the general circulation. Suprachoroidal injections of drug solutions have also been performed, but again the drug availability is short-lived. Such methods make it difficult to maintain therapeutic levels of drug for adequate time periods.

Efforts to address this problem have lead to the development of drug delivery devices, or implants, which can be implanted into the eye such that a controlled amount of desired drug can be released constantly over a period of several days, or weeks, or even months. Many such devices have been previously reported. See, for example, U.S. Pat. No. 4,853,224, which discloses biocompatible implants for introduction into an anterior segment or posterior segment of an eye for the treatment of an ocular condition. U.S. Pat. No. 5,164,188 discloses a method of treating an ocular condition by introduction of a biodegradable implant comprising drugs of interest into the suprachoroidal space or pars plana of the eye. See also U.S. Pat. Nos. 5,824,072, 5,476,511, 4,997,652, 4,959,217, 4,668,506, and 4,144,317. Other method includes anchoring a plug or tack containing a drug into the sclera of the eye (see, e.g. U.S. Pat. No. 5,466,233).

Various sites exist in the eye for implantation of a drug delivery device or implant, such as the vitreous of the eye, anterior or posterior chambers of the eye, or other areas of the eye including intraretinal, subretinal, intrachoroidal, suprachoroidal, intrascleral, episcleral, subconjunctival, intracorneal or epicorneal spaces. Wherever the desired location of implantation, typical methods of implantation all require relatively invasive surgical procedures, pose a risk of excessive trauma to the eye, and require excessive handling of the implant. For example, in a typical method for placement in the vitreous, an incision is made through the sclera, and the implant is inserted into and deposited at the desired location in the vitreous, using forceps or other like manual grasping device. Once deposited, the forceps (or grasping device) is removed, and the incision is sutured closed. Alternatively, an incision can be made through the sclera, a trocar can be advanced through the incision and then the implant can be delivered through the trocar. Similar methods can be employed to deliver implants to other locations, e.g., implantation in the anterior chamber of the eye through an incision in the cornea.

The drawbacks of such techniques for implant delivery are many-fold. Extensive handling of the implant is necessary in these techniques, creating a risk that the implant will be damaged in the process. Many such implants are polymer-based and are relatively fragile. If portions of such plants are damaged and broken-off, the effective therapeutic dose delivered by the implant once placed will be significantly altered. In addition, it becomes inherently difficult using these methods to achieve reproducible placement from patient to patient. Also of import is that fact that all such techniques require an incision or puncture in the eye large enough to require suturing. Thus, such techniques are typically performed in a surgical setting.

U.S. Pat. No. 6,899,717 provides for an ergonomically designed apparatus in which a simple manual depression of an actuator produces proportional movement of a linkage that causes an implant or micro-implant (Drug Delivery System, DDS) to be ejected through an applicator cannula and disposed at the desired location in the eye. Small gauge cannulas are provided for self-sealing methods of delivery.

However, it has been found that a DDS deposited at a desired location in the vitreous does not remain at the desired location but may track back with the applicator cannula during withdrawal of the cannula. It has been concluded that the viscous property of the vitreous humor appears to be the cause of the attraction between the DDS and the application cannula.

The present invention overcomes this problem with two mechanisms.

The first mechanism provides a stylet that pushes the DDS out from a needle into the vitreous and the second mechanism provides for the injection of a viscous material from the same stylet. The viscous material plugs up the channel of the needle in the vitreous and accordingly prevents the DDS from tracking back with the applicator cannula during withdrawal.

SUMMARY OF THE INVENTION

An embodiment of delivery system for intraocular (such as intravitreal) administration of one or more solid or semi-solid implants to the eye of a patient in accordance with the present invention may include a housing with a tip connected to one end of the housing along with a first cannula extending from the tip for inserting a rod implant into tissue.

A second cannula may be concentrically disposed within said first cannula for forcing said rod implant out of the first cannula and for ejecting a fluid behind the insertion rod implant in said tissue.

A rod implant may also be part of the present invention along with a fluid which may be a viscous material or have a viscous inducing component such as for example a polymeric high molecular weight hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

A first piston may be provided and slidably disposed within the housing along with a first plunger fixed to the first piston and also slidably disposed within the housing for ejecting the rod implant, disposed in the first cannula lumen, from the first cannula lumen by movement of the first plunger and first piston toward the tip.

A second cannula may be provided which extends from the first piston and is concentrically disposed within the first cannula and extendable through the first cannula lumen for forcing the rod implant out of the first cannula lumen as the first plunger is moved toward the tip.

A second piston may be provided and slidably disposed within the first plunger and a chamber is defined between the first piston and second piston within the first plunger. The second cannula is in fluid communication with the chamber and a second plunger, fixed to the second piston, is provided for ejecting the fluid, disposed in the chamber, through the second cannula by movement of the second plunger and the second piston toward the tip.

Preferably, the first cannula has an angulated end for facilitating penetration of tissue and the second cannula has a blunt end to facilitate engagement with the implant rod. The fluid comprises a viscous material for stabilizing the ejected rod implant.

A method in accordance with the present invention for implanting a drug delivery system rod into the vitreous of an eye generally includes disposing a drug delivery system rod into the vitreous of an eye and stabilizing a position of the rod in the vitreous by a viscous material. More particularly, the rod may be implanted through a first cannula lumen and the viscous material is ejected into the vitreous proximate the rod by a second cannula.

The method further includes using a second cannula to push the rod out of the first cannula lumen and such action is performed before ejecting the viscous material proximate the rod which may not only stabilize the rod within the viscous but also further push the rod into the vitreous.

BRIEF DESCRIPTION OF THE DRAWINGS

The advantages and features of the present invention will be better understood by the following detailed description when considered in connection with the accompanying drawings, in which:

FIG. 1 is a perspective view of an applicator in accordance with the present invention generally showing a housing, a tip connected to one end of the housing, first and second pistons, first and second cannulas, and first and second plungers;

FIG. 2 is a cross sectional view of the applicator shown in FIG. 1;

FIG. 3 is an enlarged cross sectional view of the applicator tip and cannulas illustrated in FIGS. 1 and 2;

FIG. 4 is a cross sectional view illustrating the use of the applicator in injecting a rod implant into tissue; and FIG. 5 is a view similar to FIG. 4 illustrating the stabilization of the rod within the tissue by a viscous material.

DETAILED DESCRIPTION

With reference to FIGS. 1-5, there is shown a syringe needle stylet drug delivery system intravitreal implant applicator 10 in accordance with the present invention which generally includes a housing 14 which may be formed from any suitable material and is preferably transparent in order to visualize the position of a first piston 16 and plunger 18 therein. A tip 22 is connected to one end 24 of the housing 14 by means of threads 28, or the like, (See FIG. 2) and a first cannula 30 extends from the tip 22 which includes a lumen 32 therethrough, as most clearly seen in FIG. 3. Preferably, the first cannula 30 is angulated for facilitating a penetration of vitreous 34 illustrated in FIGS. 4 and 5.

With continued reference to FIG. 3, a rod implant 38, disposed within the first lumen 32, is ejected therefrom by a second cannula 42 which extends through the first cannula lumen 32 and forces the rod implant 38 out of the first cannula lumen 32 as the first piston 16 and plunger 18 is moved toward the tip 22. This is illustrated in FIG. 4 by the arrows 46. Suitable rod implants and method of manufacturing same is set forth in U.S. patent application Ser. No. 11/859,627, filed Sep. 21, 2007 and entitled "Steroid Containing Drug Delivery Systems". This patent is to be incorporated herein in its entirety by this specific reference thereto.

Providing the second cannula 42 with a blunt end 50 facilitates ejection of the rod 38. The rod 38 and may be an intravitreal drug delivery system (DDS) such as Posurdex and the Brimonidine. A housing handle 56 and a first plunger handle 58 facilitate the manual movement of the first plunger 18 and the first piston 16 for ejecting the DDS rod 38 through the first cannula 30.

A second piston 64 is disposed within the first plunger 18 and interconnected to a second plunger 66 and handle 68. Initially defined between the first piston 16 and second piston 64 is a chamber 74 for containing any biocompatible viscous material, such as, for example, Healon.

Alternatively, the fluid may include any suitable viscosity inducing component such as, for example, but are not limited to, a polymeric high molecular weight hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

The viscosity-inducing component may be a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. Such components are described and set forth in U.S. Ser. No. 11/859,621 hereinabove referenced and incorporated herein.

In addition, the delivery of an active agent or implant described in U.S. Ser. Nos. 10/966,764, 11/741,366, 11/039, 192, 11/116,698, 11/695,527; 60/939,659 and 11/742,350 which are to be incorporated herein in their entirety by this specific reference thereto.

As illustrated, the second cannula 42 is in fluid communication with the chamber 74 for enabling ejection of the fluid, or viscous material, 78 through the second cannula 42 by movement of the second plunger 66 and second piston 64 toward the tip 22 as illustrated by the arrow 84.

As shown in FIG. 5 the viscous material 78, forced from the second cannula 42 behind the rod 38, both stabilizes the rod 38 and prevents movement thereof as the applicator 10 with cannulas 30 and 42 are withdrawn from the vitreous 34. In addition, the viscous material 78 may further force the rod 38 into the viscous 34 to a desired location.

FIGS. 4 and 5 further illustrate a method of implanting a drug delivery system rod into the vitreous of an eye in accordance with the present invention. This method generally includes disposing a drug delivery system rod into the vitreous of an eye and stabilizing a position of the rod in the vitreous by a viscous material. The rod is implanted through a first cannula lumen 32 through the use of the second cannula 42 for pushing the rod 38 out of the first cannula lumen 32.

As illustrated in FIG. 5, the viscous material 78 is injected into the vitreous 34 proximate the rod 38 via the second cannula 42. Further pushing of the rod 38 in the vitreous 34 may be accomplished by continued movement of the second piston 64 and second plunger to force more of the viscous material 78 behind the rod 38. After injecting of the viscous material 78 the applicator 10 is removed from the viscous 34.

Although there has been hereinabove described a specific drug delivery system and methods in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A drug delivery system for introducing an implant into the vitreous of an eye, said system comprising:
   a housing;
   a tip connected to one end of said housing;
   a rod implant;
   a rod stabilizing fluid;
   a first plunger and a second plunger;
   a first piston slidably disposed within said housing;
   a second piston slidably disposed within said first plunger;
   a first cannula extending from said tip for receiving said rod implant and inserting said rod implant into the vitreous of an eye following movement of said first plunger and a second cannula concentrically disposed within said first cannula; and
   a chamber within said first plunger, said chamber being defined between said first piston and said second piston, said second cannula being in fluid communication with said chamber;
   wherein said second cannula is adapted for receiving and ejecting the rod stabilizing fluid from the chamber behind the inserted rod implant upon movement of said second plunger, wherein the rod stabilizing fluid both stabilizes the inserted rod implant and prevents movement of the inserted rod implant as the cannulas are withdrawn from the vitreous of an eye.

2. The drug delivery system according to claim 1 wherein said rod stabilizing fluid includes a viscosity-inducing component.

3. The drug delivery system according to claim 2 wherein said viscosity-inducing component is selected from a group consisting of a polymeric high molecular weight hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

4. A drug delivery system for introducing an implant into the vitreous of an eye, said system comprising:
   a housing;
   a tip connected to one end of said housing;
   a rod implant;
   a rod stabilizing fluid:
   a first piston slideably disposed within said housing;
   a first cannula extending from said tip and having a lumen extending therethrough;
   a first plunger fixed to said first piston and slideably disposed within said housing, for ejecting the rod implant, disposable in the first cannula lumen, from the first cannula lumen by movement of said first plunger and first piston toward said tip;
   a second cannula, extending from said first piston and concentrically disposed within said first cannula and extendable through the first cannula lumen, for forcing said rod implant out of the first cannula lumen as the first plunger is moved toward said tip;
   a second piston slideably disposed within said first plunger;
   a chamber within said first plunger, said chamber being defined between said first piston and said second piston, said second cannula being in fluid communication with said chamber; and
   a second plunger fixed to said second piston for ejecting the rod stabilizing fluid, disposed in said chamber, through said second cannula by movement of said second plunger and second piston toward said tip, wherein the rod stabilizing fluid both stabilizes the ejected rod implant and prevents movement of the ejected rod implant as the cannulas are withdrawn from the vitreous of an eye.

5. The drug delivery system according to claim 4 wherein said first cannula has an angulated end for facilitating penetration of the vitreous of an eye and said second cannula has a blunt end to facilitate engagement with said rod implant.

6. A drug delivery system for implanting a drug delivery rod into the vitreous of an eye, the system comprising:
   a housing;
   a tip connected to one end of said housing;
   a first piston slideably disposed within said housing;
   a first cannula extending from said tip and having a lumen extending therethrough;
   an implantable drug delivery rod disposed within the first cannula lumen;
   a first plunger fixed to said first piston and slideably disposed within said housing for ejecting the drug delivery rod from the first cannula lumen as the first plunger is moved toward said tip;
   a second cannula extending from said first piston and concentrically disposed within said first cannula and extendable through the first cannula lumen for forcing said drug delivery rod out of the first cannula lumen as the first plunger is moved forward;
   a second piston slideably disposed within said first plunger;
   a chamber within said first plunger, said chamber being defined between said first piston and said second piston, said second cannula being in fluid communication with said chamber;
   a rod stabilizing fluid, disposed in the chamber, for preventing movement of the ejected drug delivery rod in the vitreous as the first and second cannulas are withdrawn from the vitreous; and
   a second plunger fixed to said second piston for ejecting the rod stabilizing fluid through said second cannula and behind the ejected drug delivery rod by movement of said second plunger and second piston toward said tip.

7. The drug delivery system according to claim 6 wherein said first cannula has an angulated end for facilitating penetration of the vitreous of an eye and said second cannula has a blunt end to facilitate engagement with said implantable rod.

8. The drug delivery system according to claim 6 wherein said rod stabilizing fluid comprises a viscous material.

9. The drug delivery system according to claim 6 wherein the rod stabilizing fluid includes a viscosity-inducing component.

10. The drug delivery system according to claim 9 wherein said viscosity-inducing component is selected from a group consisting of a polymeric high molecular weight hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

11. A method of implanting a drug delivery rod into the vitreous of an eye, said method comprising:
   disposing a drug delivery rod into the vitreous of an eye using a drug delivery system of any one of claims 1, 4 or 6.

12. The method according to claim 11 wherein said rod stabilizing fluid comprises a viscous material.

13. The method according to claim 11 wherein said rod stabilizing fluid includes a viscosity-inducing component.

14. The method according to claim 13 wherein said viscosity-inducing component is selected from a group consisting of a polymeric high molecular weight hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

15. The method according to claim 12 wherein said viscous material is used to further push the rod into the vitreous.

* * * * *